US011607356B2

(12) United States Patent
Mansfield et al.

(10) Patent No.: US 11,607,356 B2
(45) Date of Patent: *Mar. 21, 2023

(54) SYSTEMS AND TECHNIQUES FOR EVALUATING PERFORMANCE OF ACTUATOR SYSTEMS OF A PATIENT SUPPORT APPARATUS

(71) Applicant: Stryker Corporation, Kalamazoo, MI (US)

(72) Inventors: Joshua Alan Mansfield, Lawton, MI (US); Thomas Alan Puvogel, Kalamazoo, MI (US); Michael Hayes, South Haven, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/386,118

(22) Filed: Jul. 27, 2021

(65) Prior Publication Data

US 2021/0353479 A1 Nov. 18, 2021

Related U.S. Application Data

(63) Continuation of application No. 16/527,584, filed on Jul. 31, 2019, now Pat. No. 11,103,397.

(Continued)

(51) Int. Cl.
*G05B 19/042* (2006.01)
*A61G 7/018* (2006.01)
(Continued)

(52) U.S. Cl.
CPC .............. *A61G 7/018* (2013.01); *A61G 1/00* (2013.01); *A61G 5/00* (2013.01); *G05B 19/042* (2013.01);
(Continued)

(58) Field of Classification Search
CPC . A61G 7/018; A61G 1/00; A61G 5/00; A61G 2203/32; A61G 2203/30;
(Continued)

(56) References Cited

U.S. PATENT DOCUMENTS 7,398,571 B2 7/2008 Souke et al.
8,121,856 B2 2/2012 Huster et al.
(Continued)

OTHER PUBLICATIONS

U.S. Appl. No. 16/527,584, filed Jul. 31, 2019.

*Primary Examiner* — Christopher E. Everett
(74) *Attorney, Agent, or Firm* — Howard & Howard Attorneys PLLC

(57) ABSTRACT

A patient support apparatus comprises a support structure comprising a base and a patient support surface to support a patient. An actuator system facilitates movement of the patient support surface relative to a floor surface. One or more sensors are responsive to changes in position of the patient support surface caused by the actuator system. A controller is operably coupled to the one or more sensors and the actuator system. The controller is configured to operate the actuator system to move the patient support surface and to monitor the movement of the patient support surface by sensing positions of the patient support surface over time. The controller is further configured to identify a frictional load event on the actuator system during movement in a present cycle and associate the frictional load event with a sensed position of the patient support surface in the present cycle.

20 Claims, 10 Drawing Sheets

Related U.S. Application Data

(60) Provisional application No. 62/712,331, filed on Jul. 31, 2018.

(51) Int. Cl.
*A61G 1/00* (2006.01)
*A61G 5/00* (2006.01)

(52) U.S. Cl.
CPC .. *A61G 2203/32* (2013.01); *G05B 2219/2608* (2013.01)

(58) Field of Classification Search
CPC .... A61G 1/0237; A61G 1/048; A61G 1/0567; G05B 19/042; G05B 2219/2608; A61B 5/7207; A61B 5/746; A61B 5/1115; A61B 5/6892; A61B 5/1036
See application file for complete search history.

(56) References Cited

U.S. PATENT DOCUMENTS

| | | |
|---|---|---|
| 8,757,308 B2 | 6/2014 | Bhai et al. |
| 10,231,649 B2 | 3/2019 | Bhimavarapu et al. |
| 2006/0036402 A1 | 2/2006 | Deller et al. |
| 2013/0285579 A1 | 10/2013 | Kawabe et al. |
| 2016/0166453 A1 | 6/2016 | Furman et al. |
| 2019/0247257 A1 | 8/2019 | Furman et al. |
| 2020/0038270 A1 | 2/2020 | Mansfield et al. |

SYSTEMS AND TECHNIQUES FOR EVALUATING PERFORMANCE OF ACTUATOR SYSTEMS OF A PATIENT SUPPORT APPARATUS

CROSS-REFERENCE TO RELATED APPLICATIONS

The subject Patent Application is a Continuation of U.S. patent application Ser. No. 16/527,584, filed on Jul. 31, 2019, which claims priority to and all the benefits of U.S. Provisional Patent Application No. 62/712,331 filed on Jul. 31, 2018, the disclosures of each of which are hereby incorporated by reference in their entirety.

BACKGROUND

Patient support apparatuses, such as hospital beds, stretchers, cots, tables, wheelchairs, and chairs facilitate care and transportation of patients. Conventional patient support apparatuses comprise a base and a litter comprising a patient support surface upon which the patient is supported. The litter usually comprises several articulating sections, such as a back section and a foot section to facilitate care of the patient. Furthermore, the patient support surface may be adjusted (e.g., raised, lowered, articulated) between a variety of positions to allow for care and/or transportation of the patient.

Traditionally, one or more powered actuator systems are employed to adjust positions of the patient support surface by moving various components relative to each other, such as through sliding or articulating joints. When the patient support apparatus is relatively new, these joints may be efficient and allow smooth sliding and/or articulation of the various components at these joints. However, over time, the joints are susceptible to irregular wear, collect debris, build up residue, and may otherwise cause increases in frictional loads on the actuator systems. Operation of the actuator systems is adversely affected by these increases in frictional loads.

Therefore, a patient support apparatus designed to overcome one or more of the aforementioned challenges is desired.

BRIEF DESCRIPTION OF THE DRAWINGS

Advantages of the present disclosure will be readily appreciated as the same becomes better understood by reference to the following detailed description when considered in connection with the accompanying drawings wherein.

DETAILED DESCRIPTION

Figure 1:
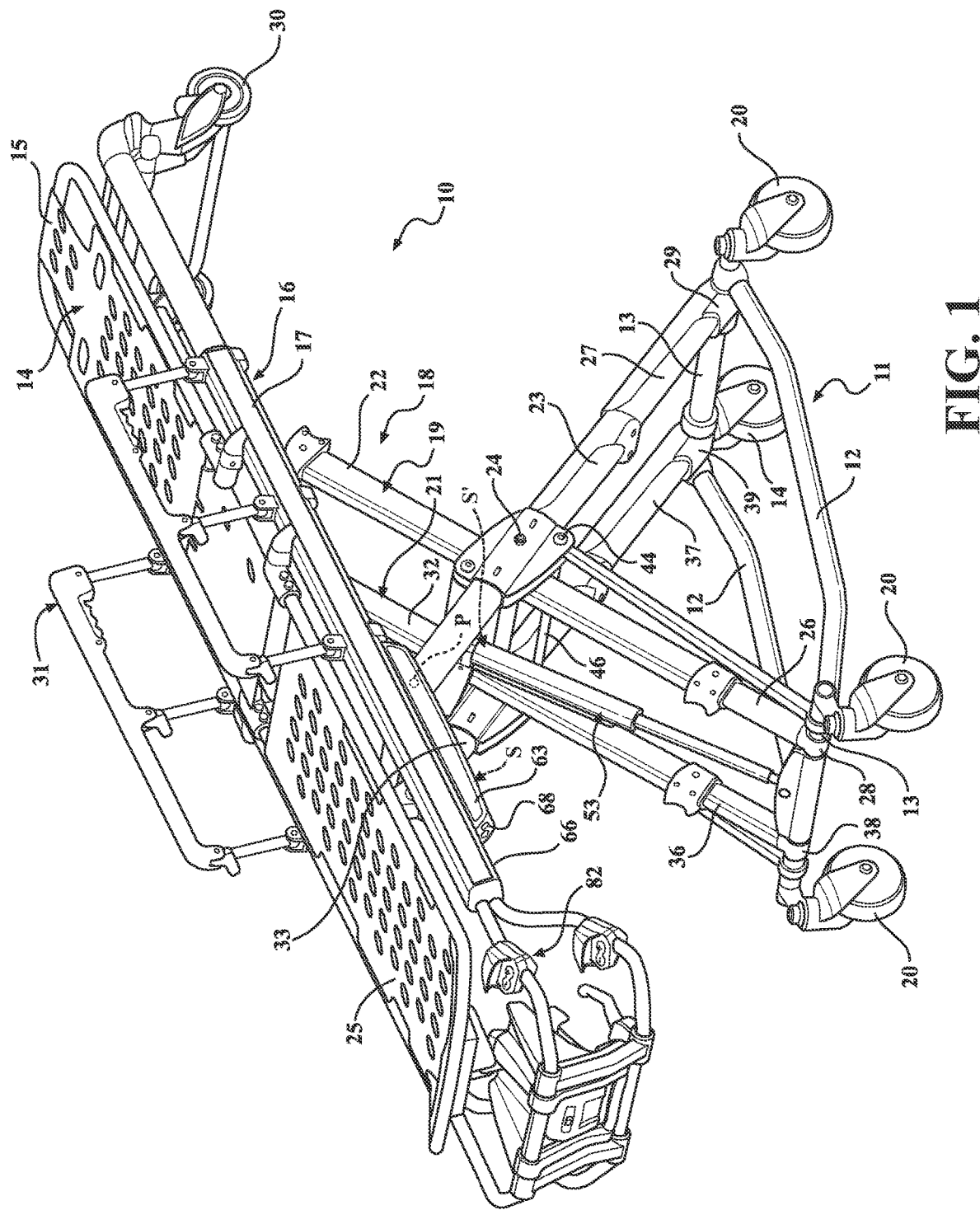
FIG. 1 is a perspective view of a patient support apparatus with an actuator system.
Figure 2A:
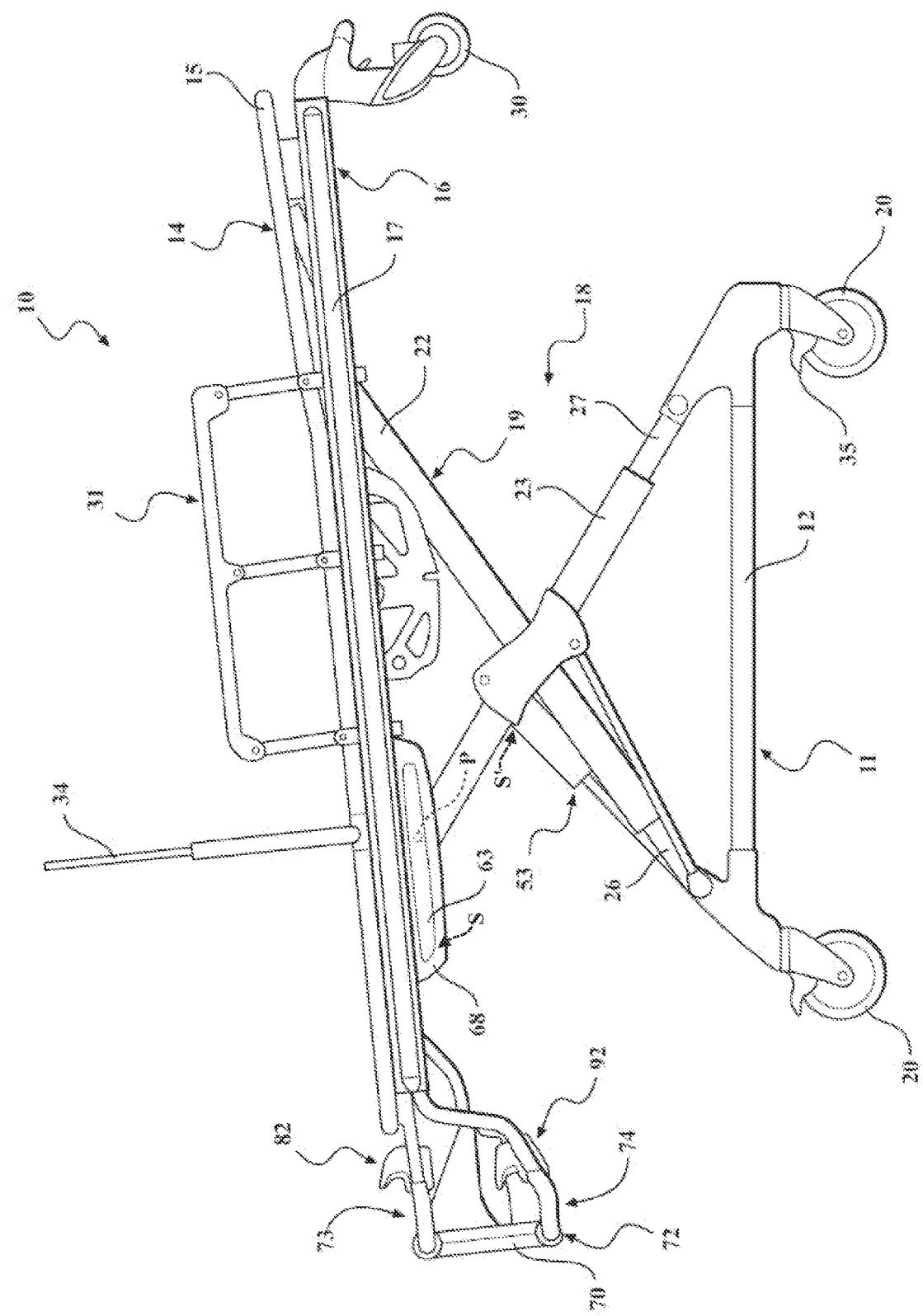
FIG. 2A is a side view of the patient support apparatus of FIG. 1 in an elevated position.
Figure 2B:
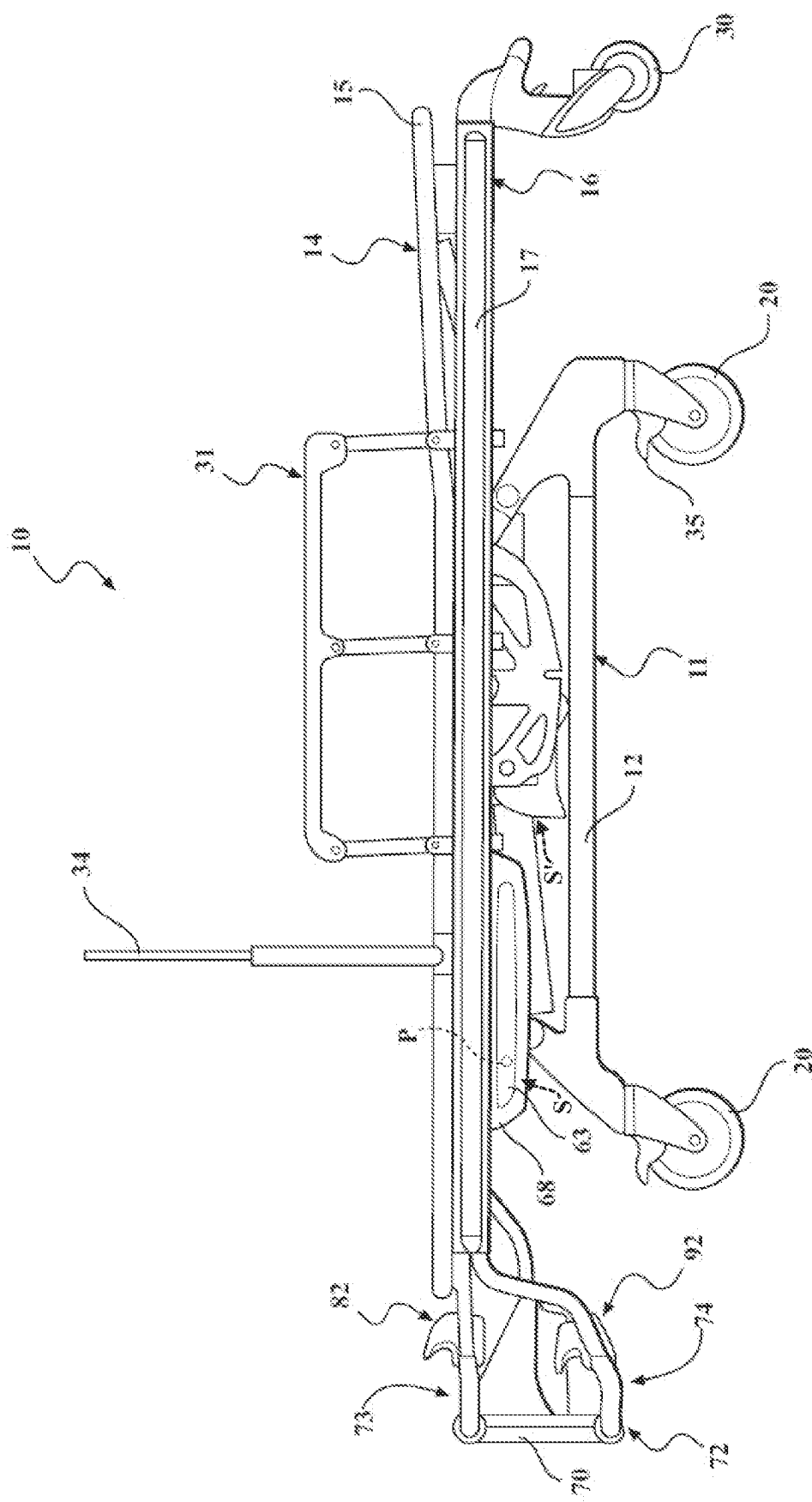
FIG. 2B is a side view of the patient support apparatus of FIG. 1 in a lowered position.

Referring to FIGS. 1-2B, a patient support apparatus 10 is shown for supporting a patient in a health care and/or transportation setting. The patient support apparatus 10 illustrated in FIGS. 1-2B comprises a cot. In other embodiments, however, the patient support apparatus 10 may comprise a hospital bed, stretcher, table, wheelchair, chair, or similar apparatus utilized in the care of a patient.

The patient support apparatus 10 comprises a support structure to provide support for the patient. The support structure comprises a base having a base frame 11. The base frame 11 may comprise longitudinally extending frame members 12 and crosswise extending frame members 13 interconnected at the ends thereof to the frame members 12 to form a rectangle. A plurality of caster wheels 20 are operatively connected proximate each corner of the rectangular shaped base frame 11 formed by the frame members 12 and 13.

The support structure further comprises a litter 16 comprising a litter frame 17. The litter 16 comprises a patient support deck having a patient support surface 14 configured to support a patient. The litter frame 17 may comprise hollow side rails 66 that extend longitudinally along the patient support surface 14. The patient support surface 14 may be comprised of one or more articulating sections, for example, a back section 15, a seat section, and a foot section 25, to facilitate care and/or transportation of the patient. The litter 16 may further comprise loading wheels 30 extending from the litter frame 17 proximate the back section 15 to facilitate loading and unloading of the patient support apparatus 10 from a vehicle. For example, the loading wheels 30 may be positioned and configured to facilitate loading and unloading of the patient support apparatus 10 into an ambulance.

Hand rails 31 may extend on opposing sides of the litter frame 17 to provide egress barriers for the patient on the patient support surface 14. The hand rails 31 may also be utilized by an individual, such as an emergency medical technician (EMT) or other medical professional, to move or manipulate the patient support apparatus 10. The hand rails 31 may comprise a hinge, pivot or similar mechanism to allow the rails 31 to be folded or stored at or below the plane of the patient support surface 14. A vertical support member 34 (see FIG. 2A) may also be attached to the litter frame 17. The vertical support member 34 may be configured to hold a medical device or medication delivery system, such as a bag of fluid to be administered via an IV. The vertical support member 34 may also be configured for the operator of the patient support apparatus 10 to push or pull on the vertical support member 34 to manipulate or move the patient support apparatus 10.

A lift mechanism 18 may be configured to interconnect the base frame 11 and the litter 16 to facilitate raising and lowering of the patient support surface 14 relative to a floor surface. The lift mechanism 18 may be manipulated to adjust the height of the litter 16 to a maximum height (see, e.g., FIG. 2A), a minimum height (see, e.g., FIG. 2B), or any intermediate height in between the maximum and minimum heights.

The lift mechanism 18 may comprise a pair of side-by-side oriented "X" frames 19 and 21. The X frame 19 comprises a pair of X frame members 22 and 23 interconnected together proximate their midpoints by means of a pivot axle 24. Each of the X frame members 22 and 23 is hollow and telescopingly receives therein a further X frame member 26 and an X frame member 27, respectively. The further X frame members 26 and 27 are supported for movement into and out of the respective X frame members 22 and 23. The distal end of the further X frame member 26 is secured via a connection 28 to the cross rail 13 at a foot end of the base frame illustrated in FIG. 1 whereas the distal end of the further X frame member 27 is connected via a connection 29 to the cross rail 13 at a head end of the base frame 11.

The X frame 21 is similarly constructed and comprises a pair of X frame members 32 and 33 which are interconnected proximate their midpoints by the axle 24. While the axle 24 is illustrated to extend laterally between the X frames 19 and 21, it is to be understood that separate axles 24 can, if desired, be employed. The X frame members 32 and 33 are hollow and telescopingly receive therein a further X frame member 36 telescopingly received in the X frame member 32 whereas a further X frame member 37 is telescopingly received in the X frame member 33. The distal end of the further X frame member 36 is connected via a connector 38 to the cross rail 13 at the foot end of the base frame 11 and the distal end of the further X frame member 37 is connected via a connector 39 to the cross rail 13 at the head end of the base frame 11. The X frame members 22, 26 extend parallel to the X frame members 32, 36 whereas the X frame members 23, 27 extend parallel to the X frame members 33, 37. While the patient support apparatus 10 illustrated throughout the drawings comprises a support structure with an X frame 19, 21, it is also contemplated that a patient support apparatus 10 may comprise a support structure and base frame 11 with a pair of front and rear folding leg members, or any other suitable structure to support the patient support surface 14 for movement.

The proximal ends P of the opposing X frame members 23 and 33 are slidably engaged with brackets 68 (only one shown on one side) attached to the underside of the side rails 66 of the litter frame 17. Each bracket 68 comprises a slot or track 63 configured to allow the proximal end P to travel along the track 63 as the lift mechanism 18 is manipulated to raise and/or lower the litter 16. The configuration or shape of the track 63 may be configured to orient the litter 16 at a particular angle as the lift mechanism 18 is raised and/or lowered. For example, the track 63 may be configured to be straight, or it may comprise one or more bends or curves, creating an S-like shape. The shape of track 63 may be configured to keep the litter 16 approximately level as the litter 16 is raised or lowered between the maximum and minimum heights. The track 63 may also be configured to tilt or angle the patient support surface 14 of the litter 16 so that either the head or leg end of the litter 16 is elevated relative to the opposing end of the litter 16 at various heights. For example, the track 63 may be configured to elevate the head end of the patient support surface 14 when raised to the maximum height to assist in loading and unloading the patient support apparatus 10 in a vehicle.

The lift mechanism 18 may further comprise an actuator system comprising one or more actuators 53, as illustrated in FIG. 1, configured to manipulate the pair of X frames 19, 21 to raise and lower the litter 16 and associated patient support surface 14 relative to the floor surface. The actuators 53 may comprise linear actuators 53. Such a lift mechanism and associated linear actuators are described in U.S. Pat. No. 7,398,571, filed on Jun. 30, 2005, entitled, "Ambulance Cot and Hydraulic Elevating Mechanism Therefor," the disclosure of which is hereby incorporated by reference.

The actuator 53, in the embodiment shown, operates to raise and lower the patient support surface 14 in the manner shown in FIGS. 2A and 2B. Notably, during this movement many components of the patient support apparatus 10 are moving relative to each other via joints, such as sliding and/or pivoting joints. For example, the X-frame members 26, 36 and 27, 37 are connected to the X-frame members 22, 32 and 23, 33 via sliding joints, the proximal ends P of the opposing X frame members 23 and 33 are sliding/rotating along tracks 63, the X-frame 19, 21 is pivoting about a pivot joint at axle 24, the X-frame members 22, 32 are pivoting about pivot joints connected to the litter 16, and so on. Each of these joints is susceptible to unexpected frictional loads over time that may be associated with irregular wear at the joints, debris being trapped in the joints, damaged joints, and the like. Such frictional loads may adversely affect operation of the lift mechanism 18 such that the actuator 53 operates inefficiently, e.g., raising and/or lowering of the patient support surface 14 is slower than desired.

The patient support apparatus 10 may comprise other devices that utilize actuators systems to move other components of the patient support apparatus. For example, as shown schematically in FIG. 3, the patient support apparatus 10 may comprise a deck adjustment device to articulate one or more sections of the patient support deck, a bed width extension device to adjust a width of the patient support surface, and a bed length extension device to adjust a length of the patient support surface. Each of these devices may utilize one or more actuators to carry out their associated movements, and much like the lift mechanism 18, may operate via one or more joints, that could also be susceptible to unexpected frictional loads over time.

Figure 3:
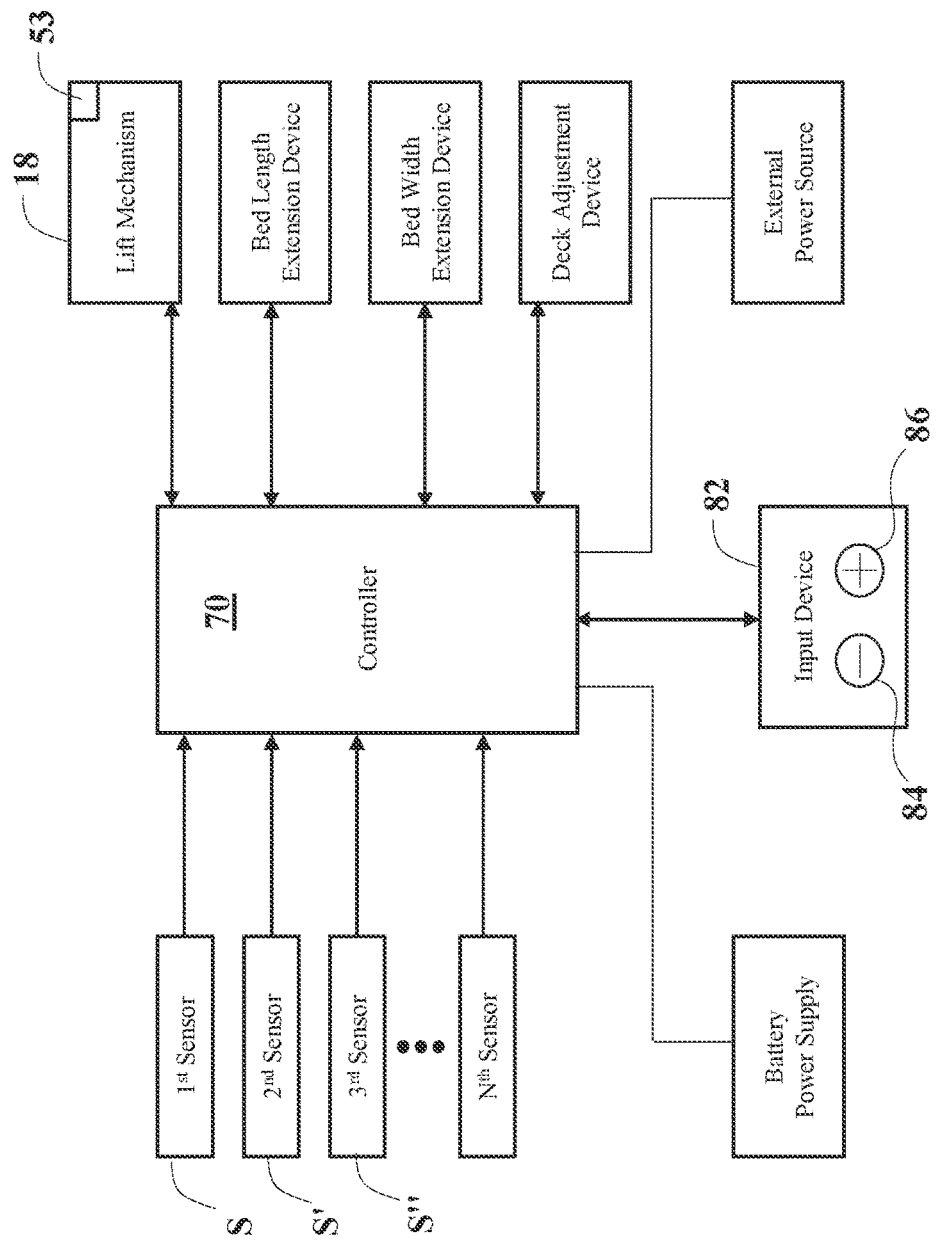
FIG. 3 is a schematic diagram of a control system.

Still referring to FIG. 3, the patient support apparatus 10 comprises a control system configured to identify unexpected frictional loads that may affect operation of the actuator systems. The control system operates to identify such frictional loads, associate the frictional loads with a position of the patient support surface 14, and compensate for the frictional loads by adjusting operation of the one or more actuator systems, as described below. It should be appreciated that the description below focuses on the actuator system comprising the actuator 53 used to raise and lower the patient support surface 14, but is equally applicable to any other actuator system that may be employed on a patient support apparatus.

As shown in FIG. 3, the control system comprises a controller 70 coupled to the lift mechanism 18. A user input device 82 is coupled to the controller 70 to trigger operation of the actuator 53 to raise and lower the patient support surface 14. The controller 70 may comprise memory configured to store data, information, and/or programs to run the routines described below. The controller 70 is operably coupled to and configured to actuate the actuator 53 of the lift mechanism 18 to raise and lower the patient support surface 14 relative to the floor surface, through any suitable control methodology, such as via pulse width modulation (PWM). The user input device 82 comprises buttons 84, 86 that may be configured to send a signal or instructions to the controller 70 to manipulate the lift mechanism 18. For example, the user input device 82 may comprise a plus (+) button 86 and a minus (−) button 84, wherein the controller 70 will receive a signal to raise the patient support surface 14 when the user presses the plus (+) button 86 or a signal to lower the patient support surface 14 when the user presses the minus (−) button 84. The user input device 82 may also comprise additional buttons configured to manipulate the patient support surface 14. In some embodiments, a second user input device may be coupled to the controller 70 (either by wire or wirelessly) to control the other powered devices of the patient support apparatus 10 described above. The user input devices may comprise any suitable user input device, such as a touchscreen with buttons (virtual), gesture-based controls, motion sensors, piezo-electric devices, foot pedals, and the like.

The controller 70 has one or more microprocessors, microcontrollers, field programmable gate arrays, systems on a chip, discrete circuitry, and/or other suitable hardware, software, or firmware that is capable of carrying out the functions described herein. The controller 70 may be carried on-board the patient support apparatus 10 (as shown), or may be remotely located. Power to the actuator system and/or the controller 70 may be provided by a battery power supply and/or an external power source. The controller 70 is operably coupled to the actuator system in a manner that allows the controller 70 to control the actuator 53. The controller 70 may communicate with the actuator system via wired or wireless connections to perform one or more desired functions.

The patient support apparatus 10 may further comprise one or more sensors S, S', S" operably coupled to the controller 70. The sensors may be optical sensors, ultrasonic sensors, laser sensors, proximity sensors, pressure sensors, load cells, encoders, potentiometers, and/or other suitable sensors for carrying out the functions described herein. The sensors may be configured to detect a plurality of parameters related to the configuration or position of the patient support apparatus 10, and to communicate with the controller 70. The sensors and the controller 70 may be configured to determine information used to generate control commands (command signals) to manipulate the patient support apparatus 10 based on a predefined set of rules and/or algorithms for interpreting signals from the sensors. The information may be stored in the controller 70 memory.

One or more of the sensors S, S', S" may be coupled to the litter 16, base 11, actuator 53, or any other suitable location on the patient support apparatus 10 to measure a position of the patient support surface 14. For example, a laser sensor or optical sensor may be attached to the underside of the litter 16 and configured to detect/measure the distance between the litter 16 and the floor surface. The distance measured by the sensor may be communicated to the controller 70 and/or determined by the controller 70. Alternatively, the position of the patient support surface 14 may be determined by a Hall effect sensor that is coupled to the actuator 53, wherein the sensor measures how far the actuator 53 has been actuated, such as by measuring rotations of a motor of the actuator 53. The one or more sensors are responsive to changes in position of the patient support surface 14 caused by the one or more actuator systems such that the controller 70 may be configured to directly or indirectly determine the position of the patient support surface 14. For example, the position of the patient support surface 14 may be associated with changes in position of any component that changes position during operation of an actuator system. Accordingly, the changes in position of such components can be considered to be changes in position of the patient support surface 14.

In some embodiments, one or more sensors S, S', S" may be placed in, along, and/or adjacent to one or more of the tracks 63 to detect a position of one or more of the proximal ends P (e.g., sliders) of the frame members 23, 33 sliding along the tracks 63 wherein the controller 70 is configured to indirectly determine the position of the patient support surface 14 based on the positions of the proximal ends P in the tracks 63. The one or more sensors S, S', S" could be linear potentiometers, Hall effect sensors, ultrasonic sensors, and the like. One example of an arrangement of Hall effect sensors in the track is described in U.S. Pat. No. 7,398,571, filed on Jun. 30, 2005, entitled, "Ambulance Cot and Hydraulic Elevating Mechanism Therefor," the disclosure of which is hereby incorporated by reference. In some versions, two, three, four, five, or more Hall effect sensors could be placed in the track to indicate discrete positions of the slider in the track, which is tied to discrete height settings, e.g., low, mid1, mid2, mid3, mid 4, mid5 . . . high, etc. In this case, the controller 70 may be able to detect frictional loads at each of the corresponding positions of the patient support surface 14 (e.g., low, mid1, mid2, mid3, mid4, mid5 . . . high, etc.) in a first cycle of operation, with the controller 70 being able to adjust operation of the actuator 53 to compensate for such frictional loads detected at the same positions in a next cycle of operation, as described in more detail below. Another example of a sensor that may be placed in the track 63 is a magnetostrictive sensor disposed in the track 63 to sense a magnet coupled to the sliders sliding in the track 63, as disclosed in U.S. patent application Ser. No. 16/271,117, filed on Feb. 9, 2018, entitled "Techniques for Determining a Pose of a Patient Transport Apparatus," which is hereby incorporated by reference. The sensor effectively senses positions of the patient support surface 14 over time by detecting movement of the sliders in the track 63.

The one or more sensors S, S', S" may also comprise feedback sensors coupled to the controller 70 and employed by the controller 70 to measure actual, current values of one or more movement parameters associated with movement of the patient support surface 14, such as position, speed, acceleration, current, voltage, or the like. For example, the feedback sensors S" may be arranged to measure rotational speed (e.g., RPM) of a motor of the actuator 53, actuation rate of the actuator 53, electrical current supplied to the actuator 53, supplied voltage, and the like.

Figure 4:
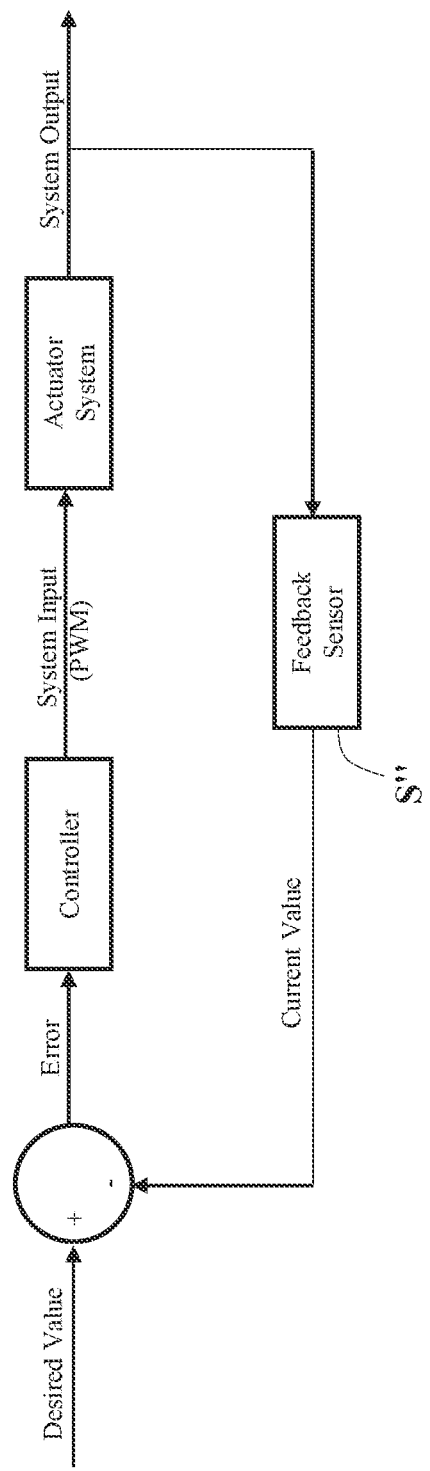
FIG. 4 is a schematic diagram of a closed loop feedback arrangement for the control system.

Referring to FIG. 4, a control loop is shown that employs one of the feedback sensors to control operation of the actuator system. In each iteration of the control loop, the controller 70 senses an instant value (e.g., measured output) of the one or more movement parameters (e.g., motor RPM) and compares the current value to a desired value to determine (e.g., calculate) an error between the current value and the desired value. If the controller 70 finds that the error is within an allowable error threshold, e.g., at or below an acceptable error value or within a range of acceptable error values, then the actuator system is working as expected. However, if the error is found by the controller 70 to be outside the allowable error threshold (e.g., exceed the acceptable error threshold or be outside of the range of acceptable error thresholds), then a frictional load event has occurred. The controller 70 thereby identifies the frictional load event based on the error and associates the frictional load event with the sensed position of the patient support surface 14 in the manner described below.

In some versions, the control loop may be capable of being switched during use to operate based on two different types of feedback. For example, the control loop may switch from a speed control configuration to electrical current limiting control configuration when the actuator system is operating under relatively high strain. Additionally, in other versions, open loop control may be employed for certain movements of the patient support surface 14, such as when the speed of the motor of the actuator 53 is being ramped up (see ramping in FIG. 5) when moving the patient support surface 14. Such open loop control of the speed may help to prevent oscillations in speed due to errors caused by friction or other factors.

Figure 5:
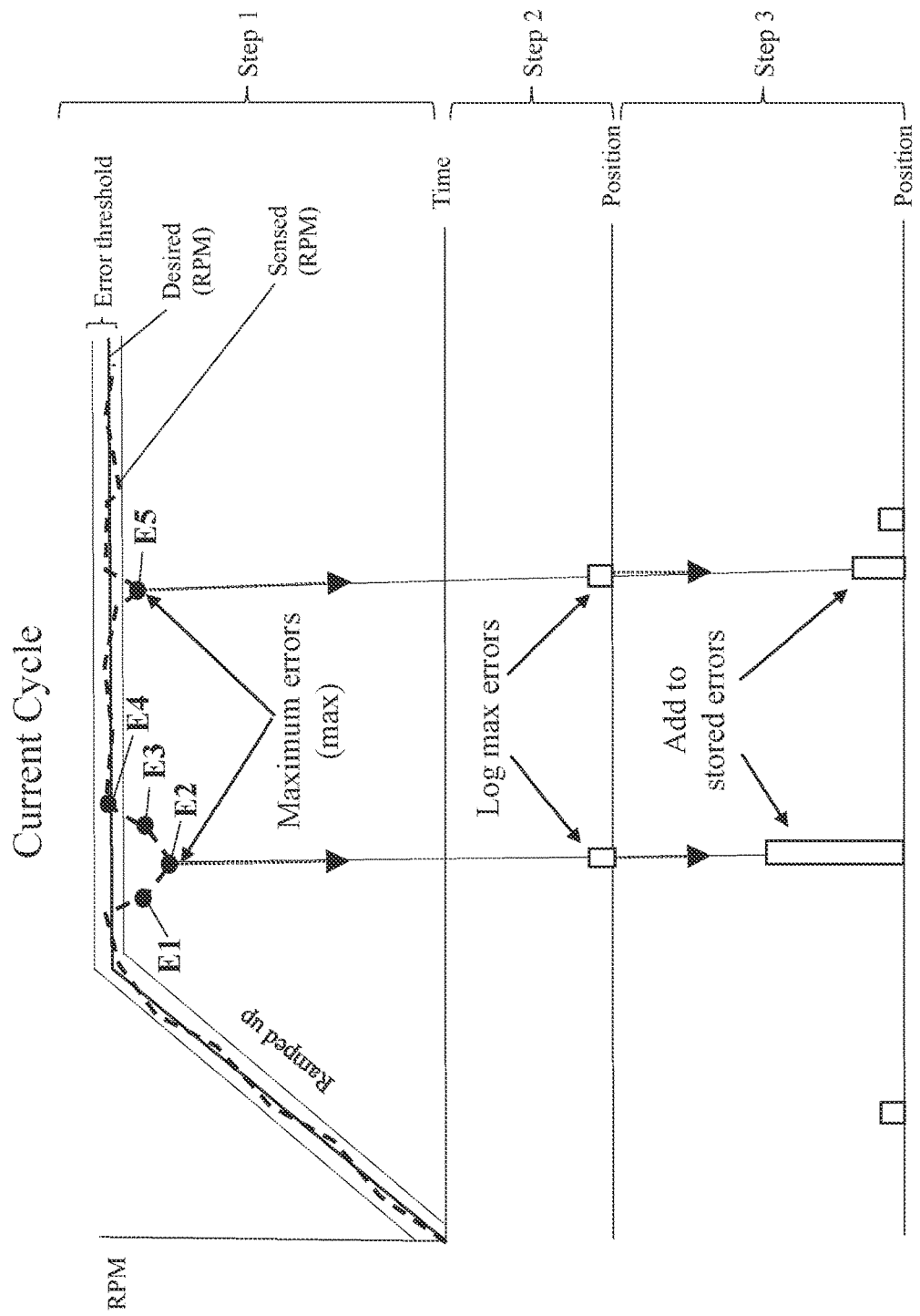
FIG. 5 illustrates a comparison of desired and actual values for a movement parameter over time to determine and log errors associated with frictional load events on the actuator system.

Referring to FIG. 5, a current cycle of movement of the patient support surface 14 is shown. As the controller 70 operates the actuator system to move the patient support surface 14 though successive positions in the current cycle, the controller 70 continuously monitors the current values of the movement parameter (e.g., sensed RPM) and compares the current values to the desired values (e.g., desired RPM) to determine errors between the current values and the desired values to determine whether frictional load events have occurred (i.e., when errors are not within the allowable error threshold) so that an error profile is established relative to the positions of the patient support surface 14. Using the process set forth below, the controller 70 identifies the maximum errors (Step 1), logs those maximum errors in memory (Step 2), and later merges those maximum errors with previously stored maximum errors to update the error profile associated with movement of the patient support surface 14 over time (Step 3). The updated error profile in Step 3 illustrates that errors are accumulating at two positions, which may indicate that persistent frictional loads are present when the actuator system moves the patient support surface 14 through those positions. Accordingly, in a next cycle, i.e., when the actuator system is operated to move through one or more of those same positions again, the controller 70 may adjust operation of the actuator system to compensate for the frictional loads.

Figure 6:
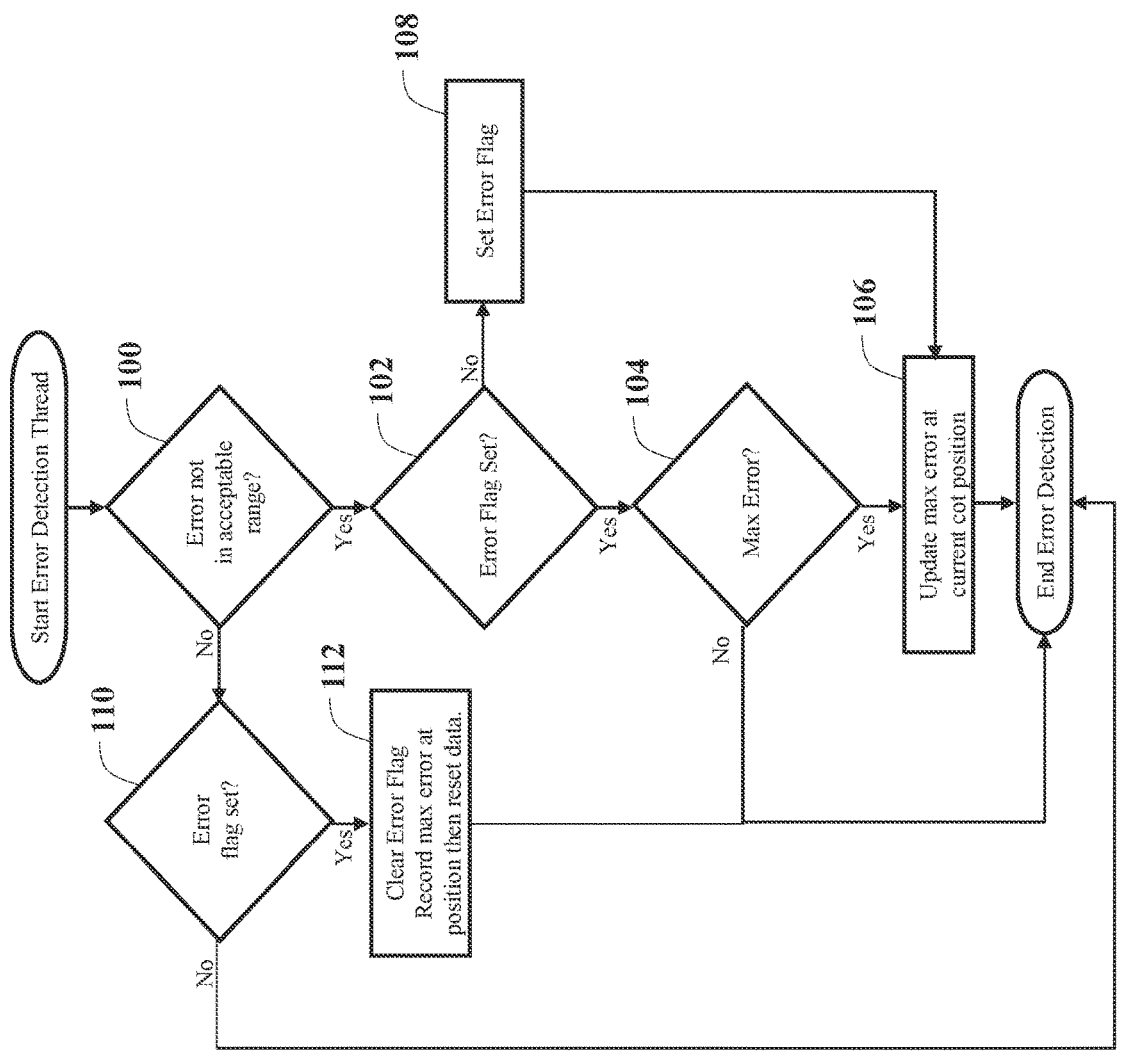
FIG. 6 is a flow chart of steps taken to detect errors associated with the frictional load events.

Referring to FIG. 6, one exemplary method of detecting the maximum errors is shown. In this routine, the error calculated by comparing the desired value to the actual value is first evaluated in step 100 to determine whether the error is outside the allowable error threshold, e.g., outside an acceptable range, which indicates that a frictional load event has occurred. If the error is outside the acceptable range, then the routine proceeds to step 102 to determine whether an error flag is currently active, such as by being set in a prior iteration. If the error flag is currently active, then the controller proceeds to step 104 and compares the current error to the prior maximum error calculated (since the same error flag was initially set) to determine if the current error is greater than the prior maximum error. If the current error is greater than the prior maximum error, then the current error is updated to become the maximum error and is associated with the current sensed position of the patient support surface 14 in step 106, i.e., a new maximum error is thus identified by the controller 70. If the error flag was not already set to active, then the error flag is set in step 108 and the controller 70 then proceeds to step 106 to set the instant error to become the maximum error, since it's the first error encountered, and is thus the maximum error. If the error determined in the control loop is not outside of the acceptable range, then in step 110 the controller 70 determines if the error flag is still active. If the error flag is not currently active, then the routine is completed. If the error flag is still active, then in step 112 the controller 70 clears/inactivates the error flag and logs the maximum error and the associated sensed position of the patient support surface 14 determined in step 106 into an error log in memory.

The controller 70 is focused on identifying maximum errors in a sequence of errors that fall outside the allowable error threshold. Referring back to FIG. 5, four errors E1, E2, E3, E4 are shown as falling outside of the allowable error threshold. However, only error E2 and error E4 are ultimately logged as maximum errors in the routine of FIG. 6. Using the sequence of errors E1, E2, E3 as an example, when the routine of FIG. 6 first analyzes error E1, the error flag is not currently active, as the prior errors were within the allowable error threshold. So, in step 108, the error flag is set to active, and in step 106 error E1 is updated to be the maximum error. In the next iteration, the routine of FIG. 6 evaluates error E2. Since the error flag is already active, the routine proceeds to step 104 where the controller 70 evaluates whether E2 is the new maximum error in the present sequence in which the error flag is active. Recall that the error flag was not active in the iteration before error E1 was evaluated, so error E2 is compared only to error E1, and since error E2 is larger, it is now updated to be the maximum error. Error E3 is similarly evaluated by comparing to errors E1 and E2 in step 104, but since E3 is smaller than E2, E2 remains as the maximum error. In the next iteration of the control loop and the next associated iteration of the routine of FIG. 6, the next error E5 falls within the allowable error threshold (e.g., within the acceptable range) and, since the error flag is still active, the routine proceeds to step 112 in which the error flag is cleared and the maximum error, error E2 is logged in the error log. In other embodiments, the controller 70 may adjust operation of the actuator system for all errors that fall outside the allowable error threshold, instead of adjusting for only the maximum error in a sequence of errors. The routine of FIG. 6 may run at every iteration of the control loop of FIG. 4, or every $n^{th}$ iteration, of the control loop of FIG. 4, where n is suitable to identify frictional load events as discussed below.

In some embodiments, the controller 70 may determine whether the instant error exceeds an alarm threshold, and if so, may cease operation of the actuator system altogether and provide an error alarm to the user, which may suggest that service should be called to repair the patient support apparatus 10. The instant error may exceed the alarm threshold when the joints are broken or the actuator system is malfunctioning beyond mere frictional load events. The user may be notified of the instant error exceeding the alarm threshold by any suitable indicator, including visual, audible, or haptic alarms.

Figure 7:
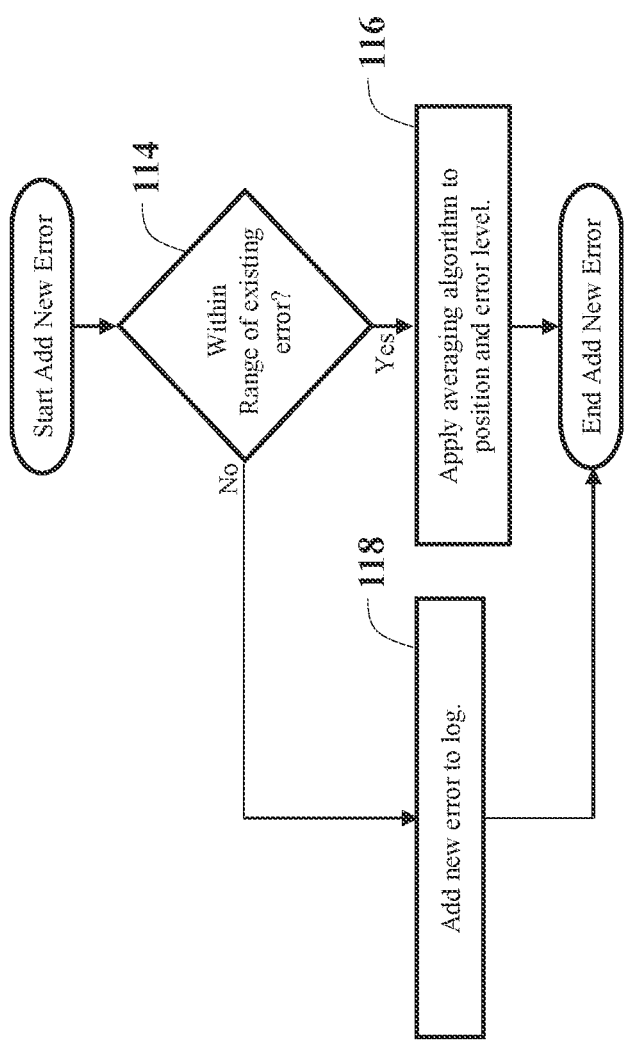
FIG. 7 is a flow chart of steps taken to manage the errors detected.

Referring to FIG. 7, once a new maximum error is logged in the error log in step 112, the controller 70 executes another routine to determine if other, previously logged maximum errors occurred at the same or similar position of the patient support surface 14. In other words, the controller 70 assesses whether multiple frictional load events occurred at the same position or a similar position of the patient support surface 14. Other, previously logged maximum errors/frictional events occurred at a "similar" position if they occurred within a predetermined threshold range or distance of the position of the patient support surface 14 sensed when the new maximum error occurred. This is determined in step 114. If other previously logged maximum errors are associated with the same or similar sensed position of the patient support surface 14, then the controller 70 averages the new maximum error and the previously logged maximum error(s) and/or the associated positions of the patient support surface 114 to determine averages in step 116. Averaging algorithms or any suitable methods of manipulating values to determine an average position and/or an average error level may be employed. If no previously logged errors occurred at the same or similar position, then a new maximum error is logged in step 118. It should be appreciated that the number of positions for which the controller 70 is analyzing errors may be finite, and comprise a predetermined number of discrete positions (e.g., low, mid1, mid2, mid3, mid 4, mid5 . . . high).

Figure 8:
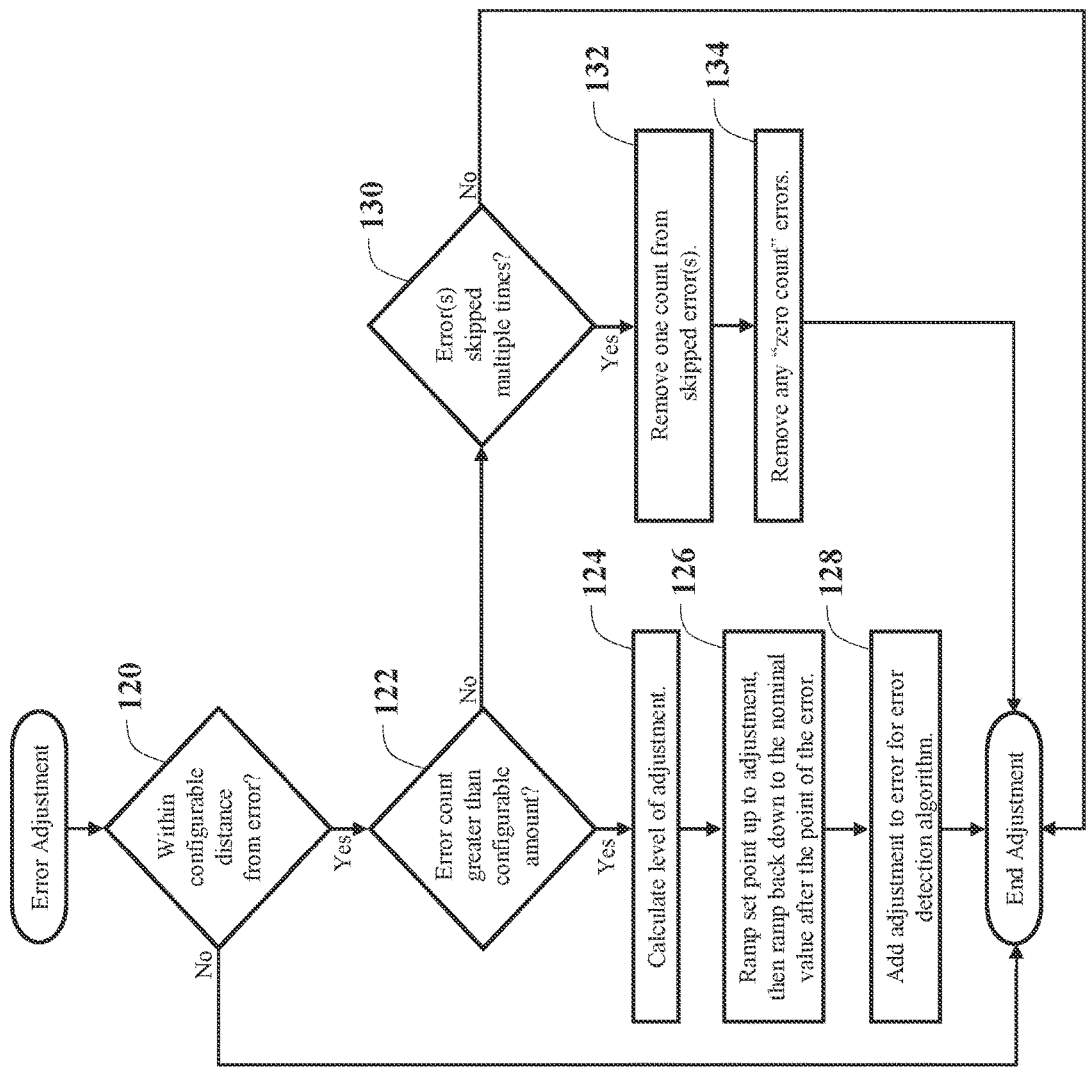
FIG. 8 is a flow chart of steps taken to adjust operation of the actuator system based on the errors detected.

Referring to FIG. 8, the controller 70 is configured to compensate for logged maximum errors (i.e., frictional load events) in an error adjustment routine that operates at each iteration of the control loop, or as desired, such as every $n^{th}$ iteration. The purpose of this routine is to adjust operation of the actuator system to account for frictional loads in subsequent cycles of movement, i.e., when the patient support surface 14 returns to the same position(s) (in its next cycle) at which the frictional loads occurred in previous cycles. In steps 120 and 122, the controller 70 first determines whether the patient support surface 14 is within a predefined distance of a position at which a maximum error occurred and whether the number of maximum errors logged for that position over a plurality of cycles exceed a predefined threshold number. The predefined distance and threshold number may be configurable and can be configured/set during manufacturing or by a user. The controller 70 may comprise a counter to count the number of maximum errors that occur at each position of the patient support surface 14.

If the present position of the patient support surface 14 is within the predefined distance of a position associated with one or more maximum errors and the number of maximum errors logged at that position meets or exceeds the predefined threshold number, then the controller 70 proceeds to step 124 to determine how much to adjust operation of the actuator system. Such adjustment may comprise adjusting the desired value (e.g., motor RPM) used for the control loop of FIG. 4 to account for the anticipated frictional loads. For example, the controller 70 may increase the motor RPM by an amount that corresponds to the distance remaining to reach the position associated with the logged maximum error(s), e.g., if within 1 inch, then the motor RPM may be increased by 10%, if within 0.1 inches, then the motor RPM may be increased by 20% and so on, such that the adjustment occurs in a ramped manner over a predetermined period of time as indicated in step 126. The controller 70 may also gradually ramp down adjustments back to the original desired value (e.g., motor RPM) for subsequent iterations of the control loop after the position associated with the frictional load events has been passed. The controller 70 utilizes the adjusted desired values in the control loop of FIG. 4. Any adjustments made to the desired value (e.g., increases to motor RPM) to compensate for frictional loads may be added to the regularly measured error in step 128 so that the control system maintains the adjustment at that particular position. Otherwise, if the error (e.g., error E2) falls below the allowable error threshold as a result of the adjustment, the controller 70 may fail to compensate again in the next cycle, i.e., when the same position is reached next time.

Still referring to FIG. 8, the controller 70 is further configured to assess whether or not the previously logged maximum errors were temporary and/or have already been corrected. In other words, occasionally, a maximum error will be logged to indicate a frictional load event, but that frictional load event may be the result of a temporary load on the patient support apparatus 10, or may have been corrected, such as by a service call or by the user. For example, if the patient support surface 14 was inadvertently trapped underneath a bumper of an ambulance during lifting, and the actuator system was temporarily unable to lift the patient support surface until the user pulled the patient support apparatus 10 away from the bumper, that would be logged as a maximum error/frictional load event, but one that would not likely re-occur in all subsequent cycles of operation. As another example, if a joint is filled with dirt and debris/residue that causes maximum errors/frictional load events for a few cycles (e.g., less than the predefined threshold number), but that joint is then cleaned, maximum errors/frictional load events may not occur in subsequent cycles. As a result, the controller 70 monitors movement of the patient support surface 14 and notes when the patient support surface 14 passes positions at which maximum errors were logged in prior cycles, but not in the instant cycle. The controller 70 also uses a counter to count the number of times that the same position is passed without logging another maximum error. In step 130, if the counter indicates that the position has been passed a predefined number of times without logging another maximum error, i.e., a predefined skipped error threshold, then the controller 70 is configured, in step 132, to remove one of the logged maximum errors from the error log in response to the frictional load being absent in the instant cycle, i.e., a skipped event. The predefined skipped error threshold may be 1, 2, 3, or more skipped events, or may be the same as the predefined threshold number mentioned above for triggering adjustment of the actuator system. In step 134, the controller 70 compares the instant count of skipped events to the instant count of maximum errors logged for the position being analyzed. If the number of skipped events is equal to the number of maximum errors that were logged for that position, then the position is considered cleared and free of frictional loads and associated maximum errors—and thus has "zero count" errors. In this case, all maximum errors logged for that position are removed from the error log and the error log is thereby cleared for that position.

Instead of removing errors in the error adjustment routine of FIG. 8, the controller 70 may conduct separate "clean-up" routines, such as during boot-up of the controller 70, or even periodically, in which the controller 70 analyzes the error log to see how many maximum errors were logged for each position, and further checks how many skipped events were logged for the same positions (i.e., how many times each position was passed free of any maximum errors being logged). The number of maximum errors and the number of skipped events are compared for each position and the controller 70 clears the error log for any positions in which the skipped events are equal to or greater than the number of maximum errors.

Figure 9:
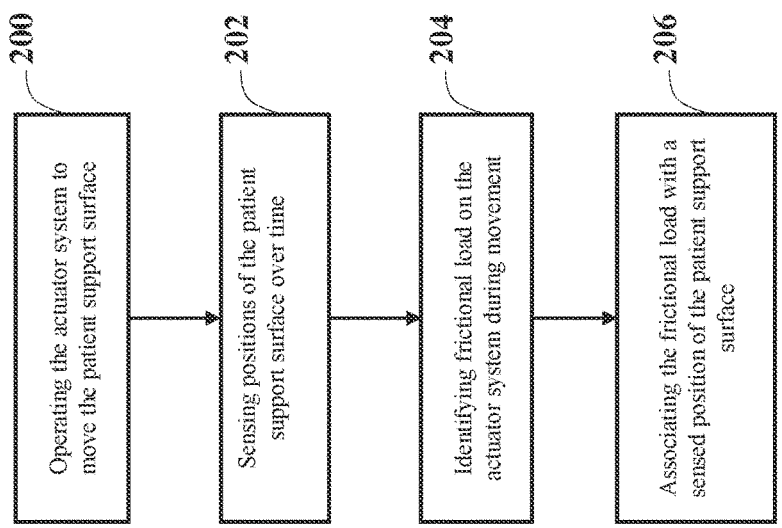
FIG. 9 is a flow chart of basic steps taken to identify frictional loads in the actuator system.

A flowchart of the basic steps carried out by the controller 70 are shown in FIG. 9. In step 200, the controller 70 operates the actuator system to move the patient support surface 14 and, in step 202, the controller 70 senses changes in position of the patient support surface 14 over time. The controller 70 then, in step 204, identifies unexpected frictional loads on the actuator system during movement that may affect operation of the actuator system. In step 206, the controller 70 associates the frictional load with a sensed position of the patient support surface 14.

In some embodiments, after assembly of the components of a new patient support apparatus 10, it may be desirable to run an initial cycle of movement of the patient support surface 14 to confirm that no post-assembly frictional load events occur, i.e., before the patient support apparatus 10 is shipped to an end user and/or before use by the end user. In this case, the errors between actual values and desired values of one or more movement parameter can be compared to an initial error threshold, which may be the same as the allowable error threshold used during normal operation in the field as previously described (e.g., see FIG. 5), or the initial error threshold could be different, such as more stringent, i.e., much lower friction is allowed in a new patient support apparatus 10 fresh off the assembly line. If the new patient support apparatus 10 fails to stay within the initial error threshold, the patient support apparatus 10 may be identified as being unsuitable for use and/or may need to be dismantled, reassembled, or the like until it stays within the initial error threshold for the entire initial cycle.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A patient support apparatus comprising:
a base arranged for movement about a floor surface;
a litter supporting a patient support deck having a patient support surface;
a lift mechanism operatively attached between the base and the litter to facilitate movement of the patient support surface relative to the floor surface, the lift mechanism including an actuator system with a linear actuator to move the patient support surface relative to the floor surface between a first configuration and a second configuration with the patient support surface spaced further from the floor surface in the first configuration than in the second configuration;
a sensor responsive to changes in position of the patient support surface caused by the actuator system; and
a controller operably coupled to the sensor and the actuator system, the controller being configured to operate the actuator of the actuator system to move the patient support surface and to monitor the movement of the patient support surface by sensing positions of the patient support surface over time, and the controller being further configured to identify a frictional load event on the lift mechanism during the movement in a current cycle between the first configuration and the second configuration in a same direction and associate the frictional load event with a sensed position of the patient support surface in the current cycle while continuing the movement in the current cycle.

2. The patient support apparatus of claim 1, wherein the controller is configured to identify the frictional load event on the lift mechanism by determining an error between a desired value of a movement parameter and an actual value of a movement parameter.

3. The patient support apparatus of claim 2, comprising one or more feedback sensors coupled to the controller to determine the actual value of the movement parameter; and wherein the movement parameter comprises one or more of position, speed, and acceleration.

4. The patient support apparatus of claim 2, wherein the controller is configured to identify the frictional load event by comparing the error to an allowable error threshold and determining that the error is outside the allowable error threshold; and wherein the allowable error threshold comprises one or more of an acceptable error value and a range of acceptable error values.

5. The patient support apparatus of claim 2, wherein the controller is configured to determine a second error in the current cycle and compare the error and the second error to identify a maximum error.

6. The patient support apparatus of claim 5, wherein the controller is configured to log the maximum error in an error log and associate the maximum error with the sensed position of the patient support surface.

7. The patient support apparatus of claim 6, wherein the controller is configured to compare the maximum error with a previously logged error associated with the sensed position of the patient support surface to determine an average error for the sensed position.

8. The patient support apparatus of claim 6, wherein the controller is configured to remove the maximum error from the error log in response to an absence of a frictional load event on the lift mechanism at the sensed position in another cycle, following the current cycle.

9. The patient support apparatus of claim 2, wherein the controller is configured to compensate for the frictional load event by adjusting operation of the actuator system in the same direction in a next cycle, following the current cycle.

10. The patient support apparatus of claim 9, wherein the controller is configured to adjust operation of the actuator system by adjusting the desired value of the movement parameter to a ramped value for a predetermined period of time and then returning to the desired value.

11. The patient support apparatus of claim 1, wherein the controller comprises a counter to count a number of frictional load events that occur at the sensed position of the patient support surface over a plurality of cycles, the controller being configured to compensate for the frictional load event by adjusting operation of the actuator system in the same direction in a next cycle if the number of frictional load events meets or exceeds a threshold number.

12. The patient support apparatus of claim 11, wherein the controller is configured to determine, during the next cycle, when the patient support surface is within a predefined distance of the sensed position at which one or more frictional load events occurred, and to begin adjusting operation of the actuator system when the patient support surface is within the predefined distance of the sensed position.

13. The patient support apparatus of claim 1, wherein the sensor includes a magnetostrictive element and an emitter arranged to determine the changes in position of the patient support surface caused by the lift mechanism.

14. The patient support apparatus of claim 13, wherein the emitter comprises a magnet.

15. The patient support apparatus of claim 13, wherein the magnetostrictive element is operatively attached to the litter to sense movement of the emitter relative to the litter.

16. The patient support apparatus of claim 1, wherein the linear actuator comprises a hydraulic actuator.

17. The patient support apparatus of claim 1, further comprising a user input device coupled to the controller to facilitate operation of the actuator system based on user input.

18. The patient support apparatus of claim 1, wherein the lift mechanism further includes a frame member pivotably coupled to the litter.

19. The patient support apparatus of claim 1, wherein the lift mechanism further includes a frame member slidably and pivotably coupled to the litter; and wherein the sensor is arranged to determine the changes in position of the patient support surface based at least partially on sliding movement of the frame member relative to the litter.

20. The patient support apparatus of claim 1, wherein the lift mechanism further includes a frame member pivotably coupled to the base.

* * * * *